United States Patent
Roche et al.

(10) Patent No.: US 9,393,324 B2
(45) Date of Patent: Jul. 19, 2016

(54) USE OF 31P NMR SPECTROSCOPY OF WHOLE HEART ENERGETICS FOR DETECTION OF DRUG-INDUCED CARDIOTOXICITY

(71) Applicant: Battelle Memorial Institute, Columbus, OH (US)

(72) Inventors: Brian M. Roche, Upper Arlington, OH (US); Kim A. Henderson, Columbus, OH (US)

(73) Assignee: Battelle Memorial Institute, Columbus, OH (US)

( * ) Notice: Subject to any disclaimer, the term of this patent is extended or adjusted under 35 U.S.C. 154(b) by 476 days.

(21) Appl. No.: 13/908,025

(22) Filed: Jun. 3, 2013

(65) Prior Publication Data

US 2013/0323175 A1 Dec. 5, 2013

Related U.S. Application Data

(60) Provisional application No. 61/655,155, filed on Jun. 4, 2012.

(51) Int. Cl.
*A61K 49/00* (2006.01)

(52) U.S. Cl.
CPC .......... *A61K 49/0004* (2013.01); *A61K 49/0008* (2013.01)

(58) Field of Classification Search
None
See application file for complete search history.

(56) References Cited

PUBLICATIONS

Bristow MR. Beta-adrenergic receptor blockade in chronic heart failure. 2000 Circulation 101: 558-569.*
Azim, H.A., et al., "Long-term toxic effects of adjuvant chemotherapy in breast cancer," Ann Oncol., 2011, pp. 1939-1947, vol. 22(9).
Bittner, V., et al., "31P NMR spectroscopy in chronic adriamycin cardiotoxicity," Magn. Reson. Med., 1991, pp. 69-81, vol. 17.
Force, T. et al., "Cardiotoxicity of kinase inhibitors: The prediction and translation of preclinical and translation of preclinical models to clinical outcomes," Nat. Rev. Drug Discov., 2011, pp. 111-126, vol. 10(2).
Hancock, C.R., et al., "$^{31}$P-NMR observation of free ADP during fatiguing, repetitive contractions of murine skeletal muscle lacking AK1," Am. J. Physiol. Cell. 1 Physiol., Feb. 2, 2005, pp. C1298-C1304, vol. 288.
Hays, P.A., et al., "A processing method enabling the use of peak height for accurate and precise proton NMR quantitation," Magnetic Resonance in Chemistry, 2009, pp. 819-824, vol. 47.
Hernandez-Esquivel, L., et al., "Cardiotoxicity of copper-based antineoplastic drugs casiopeinas is related to inhibition of energy metabolism," Science Direct, Toxicology and Applied Pharmacology, 2006, pp. 79-88, vol. 212.
Holsapple, et al., "Modernizing Toxicity for Drug Development," Drug Discovery and Development, Apr. 12, 2012, pp. 22-24 vol. 15, No. 4.
Maslov, M.Y., et al., "Reduced in vivo high-energy phosphates precede adriamycin-induced cardiac dysfunction," American Journal of Physiology—Heart and Circulatroy Physiology, 2009, pp. H332-H337, vol. 299.
Murphy, E., et al., "NMR observability of ATP: Preferential depletion of cytosolic ATP during ischemia in perfused rat lived," Biochemistry, 1988, pp. 526-528, vol. 27.
Sarazan, R.D., et al., "Cardiovascular function in nonclinical drug safety assessment: Current issues and opportunities," Int. J. Toxicol., 2011, pp. 272-286, vol. 30(3).
Sarszegi, Z., et al., "BGP-15, a PARP-inhibitor, prevents imatinib-induced cardiotoxicity by activating Akt and suppressing JNK and p38 MAP kinases," Mol. Cell Biochem., 2012, pp. 129-137, vol. 365, Springer.
Zeglinski, M. et al., "Trastuzamab-induced cardiac dysfunction: A 'dual-hit'," Exp. Clin. Cardiol., 2011, pp. 70-74, vol. 16(3).

* cited by examiner

*Primary Examiner* — Michael G Hartley
*Assistant Examiner* — Jennifer Lamberski
(74) *Attorney, Agent, or Firm* — Frost Brown Todd LLC

(57) ABSTRACT

Disclosed are methods of determining cardiac toxicity of a compound of interest, wherein a heart or cardiac cell of a mammal may be contacted a compound of interest and peak levels of one or more indicators of cardiac energetics after administration of the compound may be detected using $^{31}$P NMR before and after exposure to a compound known to stress the heart or cardiac cell. Detection of the indicators of cardiac energetics may be combined with other indicators of cardiac function such as, for example, contractility, relaxation, heart rate, and/or conduction velocity to arrive at a profile capable of predicting the cardiotoxicity of potential therapeutics.

11 Claims, 7 Drawing Sheets

US 9,393,324 B2

USE OF 31P NMR SPECTROSCOPY OF WHOLE HEART ENERGETICS FOR DETECTION OF DRUG-INDUCED CARDIOTOXICITY

This application claims priority to U.S. Patent Application Ser. No. 61/655,155, filed Jun. 4, 2012, the entirety of which is incorporated herein by reference.

BACKGROUND OF THE INVENTION

Current approaches to toxicity testing and safety assessment rely on traditional studies that evaluate observable outcomes in whole animals, such as clinical signs or pathological changes that are indicative of a disease state, and have changed very little over the last several decades. (See., e.g., Modernizing Toxicity for Drug Development, Hosapple, et al., Drug Discovery and Development, Apr. 12, 2012.) However, despite the methods currently used to screen potential therapeutics, more than 30% of drugs are eventually removed from the market due to adverse cardiac effects.

Accordingly, cardiotoxicity has become a central focus of drug development. Defining the relationship between molecular and adverse events so that researchers can identify and characterize the critical pathways involved with pathologies and organ system failures is of emerging importance in drug development. Accordingly, there is a need in the art to define such relationships so as to allow improved drug development.

BRIEF SUMMARY

In one aspect, methods of determining cardiac toxicity of a compound of interest are disclosed. The disclosed methods may include the step of determining peak levels of inorganic phosphate, phosphocreatine, ATPγ, or a combination thereof, before and after administration of the compound of interest to a heart or cardiac cell of a mammal, using, for example, $^{31}P$ NMR, with or without concurrent measurement of functional cardiac parameters. In one aspect, the methods may be used to detect an increase, decrease, or combination thereof of inorganic phosphate, phosphocreatine, ATPγ, or a combination, wherein the increase, decrease, or combination indicates that the compound of interest is cardiotoxic. The step of measuring known biomarkers, for example, TNFα, may also be carried out in combination with the described methods.

DETAILED DESCRIPTION

Figure 1:
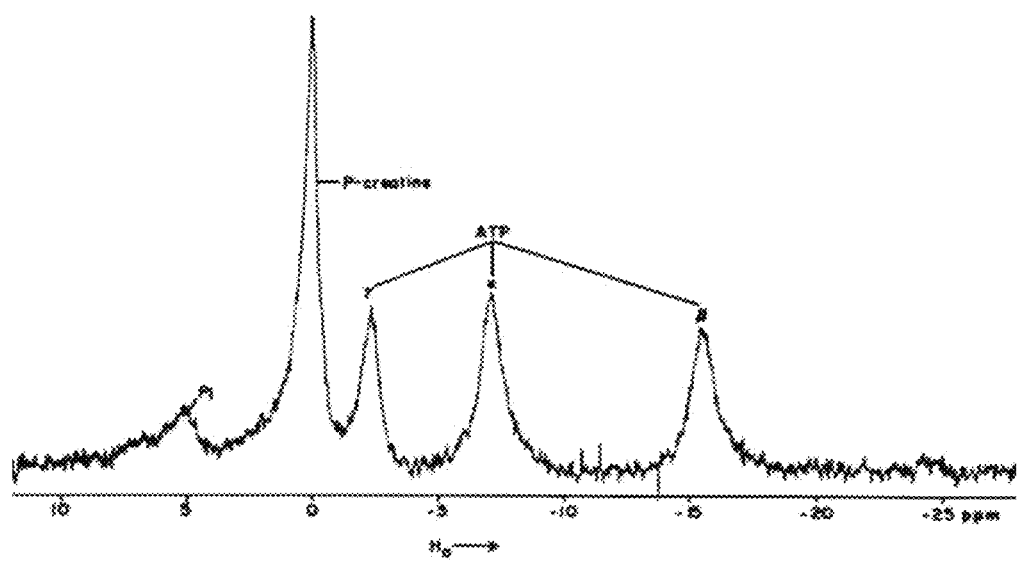
FIG. 1. High energy phosphogen spectrum.

By using integrated in vivo, ex vivo, and in vitro assessments, it is believed that the cardiotoxicity of a potential new therapeutic can be predicted without the need for long term exposure and permanent risk to patients.

In one aspect, the instant disclosure describes methods for use in determining cardiotoxicity of a potential therapeutic agent using a combination of traditional measurements of whole heart functionality together with measurements of cardiac energetics to obtain a therapeutic signature that will be predictive of cardiac toxicity. This is believed to ultimately provide for a new and more thorough evaluation of new therapeutics that allows elimination of potential cardiotoxic agents earlier in the drug discovery pipeline.

DEFINITIONS

Unless defined otherwise, technical and scientific terms used herein have the same meaning as commonly understood by one of ordinary skill in the art to which this invention belongs.

For purposes of the present invention, the following terms are defined below.

The articles "a" and "an" are used herein to refer to one or to more than one (i.e., to at least one) of the grammatical object of the article. By way of example, "an element" means one element or more than one element.

The terms "drug," "pharmaceutically active agent," "bioactive agent," "therapeutic agent," and "active agent" may be used interchangeably and refer to a substance, such as a chemical compound or complex, that has a measurable beneficial physiological effect on the body, such as a therapeutic effect in treatment of a disease or disorder, when administered in an effective amount. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

As used herein, the term "heart or cardiac cell" may refer to ex vivo applications utilizing isolated hearts (such as in the examples described herein), cardiac cells, and/or cardiac tissue comprising cardiac cells. The term may apply to heart or cardiac cells in vivo or in vitro, including cardiac tissue comprising cardiac cells, isolated from the organism of interest. The methods disclosed herein may be suitable for both in vivo and in vitro applications to whole heart, cardiac cells, including cardiac tissue, or any portion thereof which permits assessment of the relevant parameters described herein.

The practice of the present invention will employ, unless otherwise indicated, conventional techniques of molecular biology (including recombinant techniques), microbiology, cell biology and biochemistry, which are within the skill of the art.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified. All numerical ranges as used herein, whether or not expressly preceded by the term "about," are intended and understood to be preceded by that term, unless otherwise specified. All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

Any reference to a singular characteristic or limitation of the present disclosure shall include the corresponding plural characteristic or limitation, and vice versa, unless otherwise specified or clearly implied to the contrary by the context in which the reference is made.

All references cited herein are incorporated in their entirety by reference.

REFERENCES CITED

Sarazan R D, et al. Cardiovascular function in nonclinical drug safety assessment: Current issues and opportunities. *Int J Toxicol.* 2011; 30(3):272-86.

Azim H A, et al. 2011. Long-term toxic effects of adjuvant chemotherapy in breast cancer. *Ann Oncol.* 2011; 22(9): 1939-47.

Force T, Kolaja K. Cardiotoxicity of kinase inhibitors: The prediction and translation of preclinical and translation of preclinical models to clinical outcomes. *Nat Rev Drug Discov.* 2011; 10(2):111-26.

Zeglinski M, et al. Trastuzamab-induced cardiac dysfunction: A 'dual-hit'. *Exp Clin Cardiol.* 2011; 16(3):70-4.

Reference is now made in detail to particular embodiments of the methods. The disclosed embodiments are not intended to be limiting of the claims. To the contrary, the claims are intended to cover all alternatives, modifications, and equivalents.

The Multi-Scale Toxicology Initiative (MSTI) is a predictive systems toxicology approach established to define the relationship between molecular and adverse events. By defining these relationships, it may be possible for researchers to identify and characterize critical pathways involved with pathologies and organ system failures.

Because cardiotoxicity testing has become a central focus of drug development (Sarazan et al.), it is being used to more fully illustrate the MSTI approach. MSTI's experimental approach uses prototypical drugs that cause cardiac injury through known mechanisms such as isoproteranol (beta adrenergic receptor stimulation), carbony cyanide 4-(trifluoromethoxy) phenylhydrazone (FCCP, mitochondrial toxin), and verapamil (L-Type $Ca^{2+}$ channel inhibitor); and drugs that cause cardiac injury through unknown mechanisms such as doxorubicin, 5-fluorouracil, trastuzamab, sunitinib, lapatinib, and erlotinib. (Azim et al, Force, et al., Zeglinski et al.). Ideally, as a critical step in the drug identification process, it would be possible to determine functional and molecular changes associated with known toxicants in acute exposures by assaying for short-term effects (for example, effects which occur from about 20 to about 120 minutes) and sub-acute exposures for longer term effects (for example, effects that occur between 1 to 14 days) after dosing by combining multi-scale analyses. MSTI utilizes ex vivo and in vivo rat models to assay for drug-induced changes in left ventricular pressure (e.g., utilizing dP/dt as an indicator of contractility), ECG, biomarkers of injury, and whole heart energetics.

Disclosed herein are methods of determining cardiac toxicity of a compound of interest. The methods may comprise the steps of i) determining in a heart or cardiac cell of a mammal peak levels of one or more indicators of cardiac energetics selected from inorganic phosphate, phosphocreatine, ATPγ, or a combination thereof; and ii) one or more indicators of cardiac function selected from contractility, relaxation, heart rate, conduction velocity, or a combination thereof prior to contact of a compound of interest to the heart or cardiac cell.

After contacting the heart or cardiac cell with a compound of interest, such as a potential therapeutic agent, the peak levels of the one or more indicators of cardiac energetics and, optionally, one or more indicators of cardiac function such as contractility, relaxation, heart rate, conduction velocity, or a combination thereof, are measured to obtain a profile of cardiac energetics and/or function after administration. In one aspect, the one or more indicators of cardiac energetics may be obtained using $^{31}P$ NMR, such method being well known and well within the skill of one of ordinary skill in the art. (See, e.g., Murphy, E., Gabel, S. A., Funk, A. and London, R. E. 1988. NMR observability of ATP: Preferential depletion of cytosolic ATP during ischemia in perfused rat liver. *Biochemistry.* 27:526-528.)

The heart or cardiac cell of the mammal may then be contacted with an agent known to cause an increase in cardiac function, or, in other words "stress" the heart. Such function may include, for example, contractility, relaxation, heart rate, conduction velocity, or a combination thereof. In one aspect, the agent may be, for example, a beta agonist such as isoproteranol.

Following exposure to the agent known to cause an increase in cardiac function (i.e., that agent which causes "stress" to the heart), the peak levels of the one or more indicators of cardiac energetics may then be determined. One or more indicators of cardiac function may also be determined to yield a collective data set of energetic and functional parameters, thereby providing a "profile" for the compound of interest. By comparing the levels of one or more indicators prior to contact with an agent known to cause an increase in cardiac function with those levels obtained after contact with such agent, one may determine whether the compound of interest is depleting cardiac reserves and has, or is likely to have, a cardiotoxic effect.

In one aspect, a decrease in one or more indicators of cardiac energetics after administration of an agent known to "stress" the heart as compared to baseline levels may indicate that the compound of interest does, or is likely to have, cardiotoxic properties. For example, a decrease in phosphocreatine and ATPγ after exposure to the compound of interest and the agent known to cause an increase in cardiac function may indicate that said compound of interest is cardiotoxic.

In further aspects, the steps outlined above may further be combined with the step of measuring a biomarker known to be associated with cardiotoxicity. Such marker may be, for example, TNFα. Such biomarkers and the measurement thereof are also known and within the skill of one of ordinary skill in the art.

In one aspect, the time period between administration of the compound of interest and the agent known to increase cardiac function (i.e., the cardiac "stressor") is at least about 5 minutes, at least about 10 minutes, at least 20 minutes, at least 30 minutes, at least 45 minutes, or at least about one hour.

Applicants have found that by integrating whole heart energetic imaging and biomarker analysis with the Langendorff isolated heart studies, information on drug-induced changes in oxidative ATP synthesis with real-time measures of indicators of injury and contractility can provide specific insight into the mechanism (e.g., mitochondrial oxidation) of cardiac toxicity.

Applying this approach, a perfused isolated heart may be inserted into an 11.5 tesla NMR magnet for spectroscopic analysis of high-energy phosphagens (ATP, phosphocreatine, and inorganic phosphate) in combination with collection of heart effluent and tissue, and functional assessment of contractility can be determined as measured by $dP/dt_{max}$ and $dP/dt_{min}$, left ventricular developed pressure, heart rate, etc.

In combination with the functional assessment, whole heart energetics can be determined, measured as the changes in peak levels of ATP, phosphocreatine, and inorganic phosphate using NMR spectroscopy. The whole heart energetics data may serve as an early and sensitive marker of drug induced cardiac toxicity, and is advantageous for detecting cardiac toxicity because it offers a molecular marker that can be more sensitive than standard cardiac function parameters. This is supported by the disclosed data demonstrating that with the isolated rat heart, the drug doxorubicin, a chemotherapy known to cause acute and latent cardiac toxicity, decreases inorganic phosphate levels while increasing contractility parameters. In response to a stress test done by administering isoproteranol, doxorubicin hearts show a pronounced drop in phosphocreatine while control hearts do not, demonstrating that doxorubicin has caused an energy imbalance that is only revealed by the whole heart energetics NMR spectra and not by contractility alone.

The use of whole heart energetics as a biomarker to demonstrate early signs of drug induced cardiotoxicity and predict the possibility of latent toxicity fills a major gap in preclinical drug safety testing, as well as the possibility of using it to detect early signs of toxicity in patients undergoing chemotherapy.

EXAMPLES

The following Examples are provided to illustrate certain aspects of the present invention and to aid those of skill in the art in practicing the invention. These Examples are in no way to be considered to limit the scope of the invention in any manner.

Example I

Figure 2:
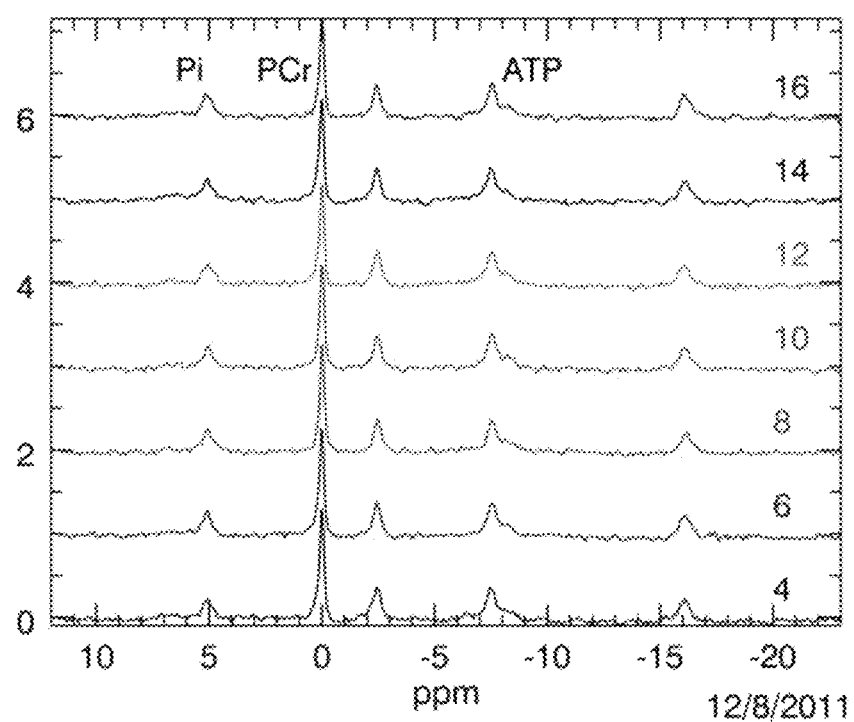
FIG. 2. Consecutive high energy phosphogen spectra from control heart.
Figure 3A:
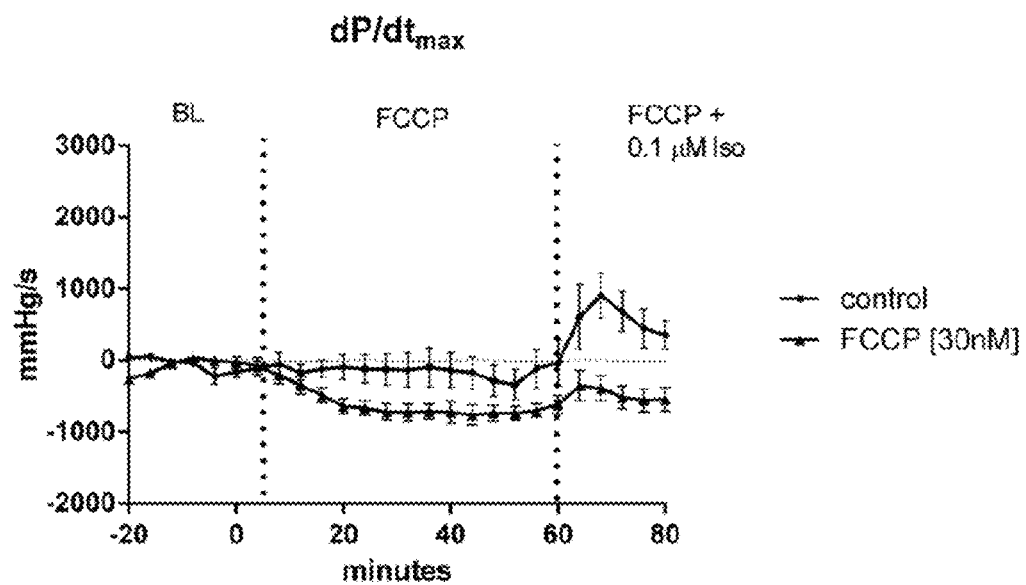
FIG. 3a-d. Effects of FCCP on contractility (dP/dtmax, FIG. 3a) and energetic (Pi,(FIG. 3b) PCr, (FIG. 3c) ATP (FIG. 3d).
Figure 3B:
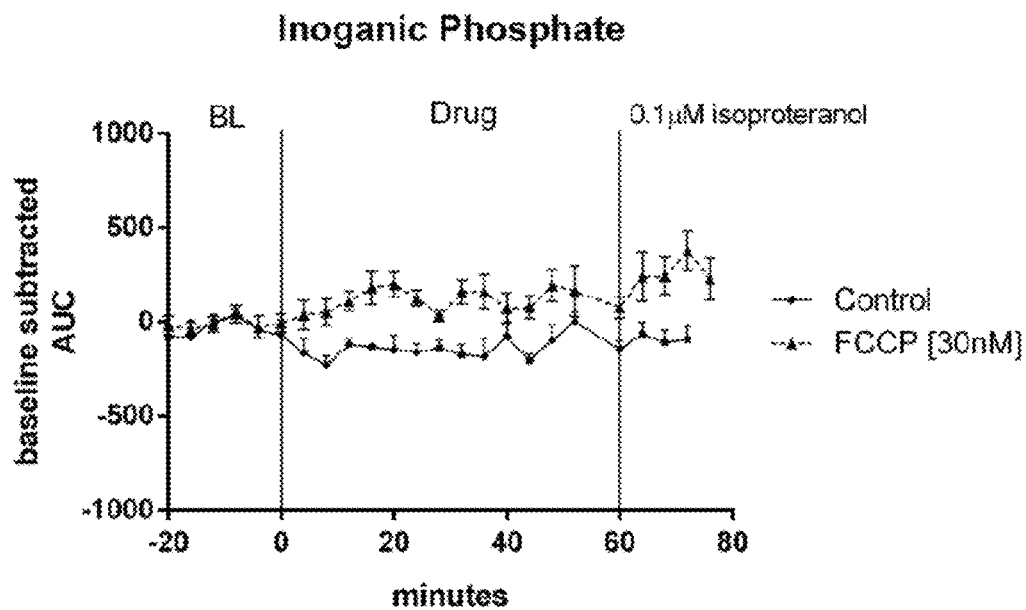
Figure 3C:
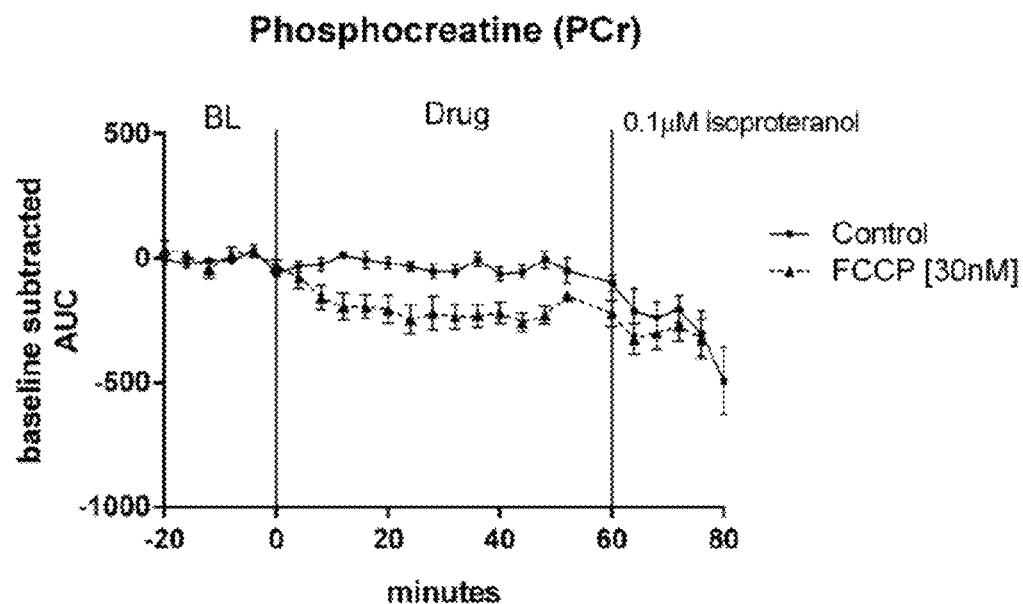
Figure 3D:
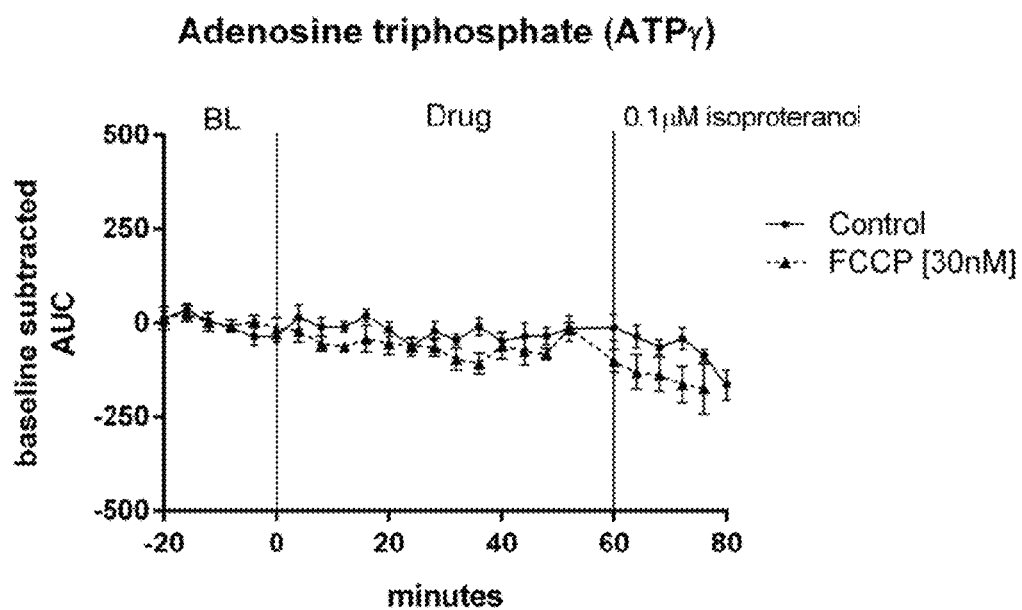
Figure 4A:
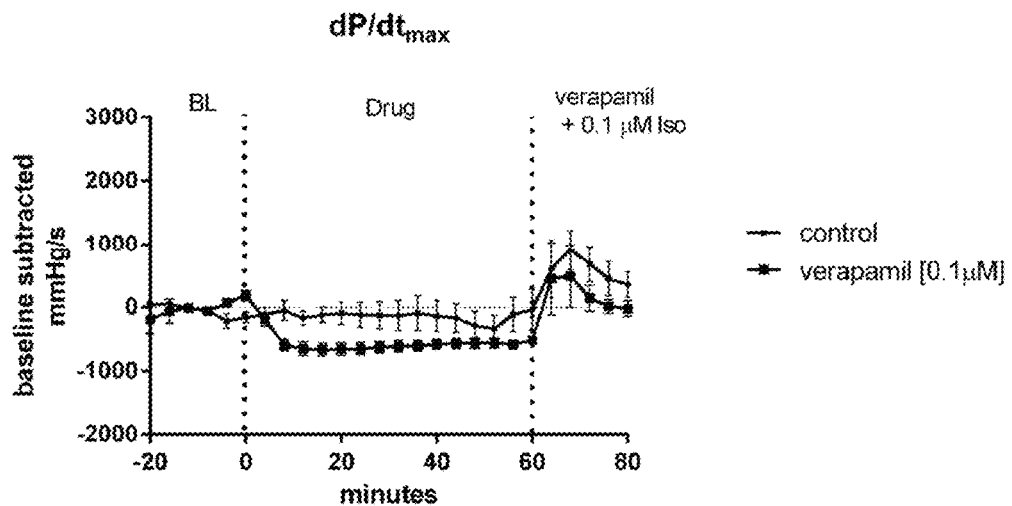
FIG. 4a-d. Effects of verapamil on contractility (dP/dtmax, FIG. 4a) and energetic (Pi,(FIG. 4b) PCr, (FIG. 4c) ATP (FIG. 4d).
Figure 4B:
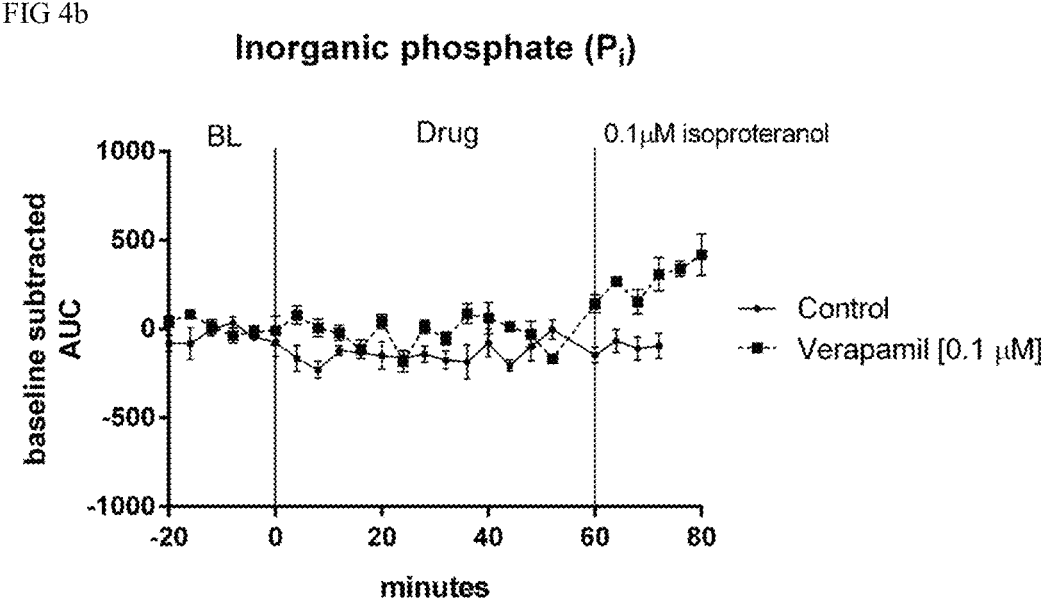
Figure 4C:
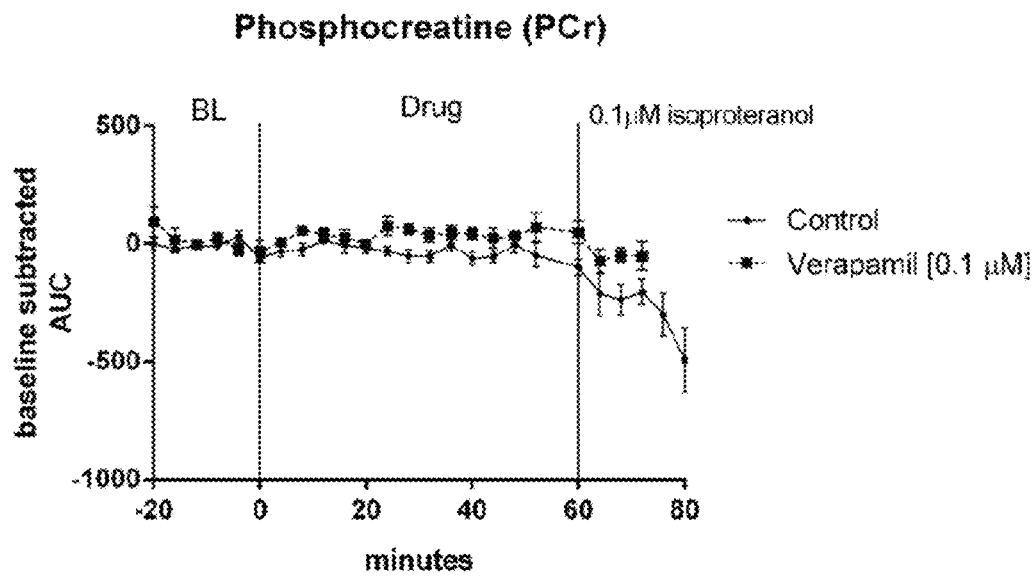
Figure 4D:
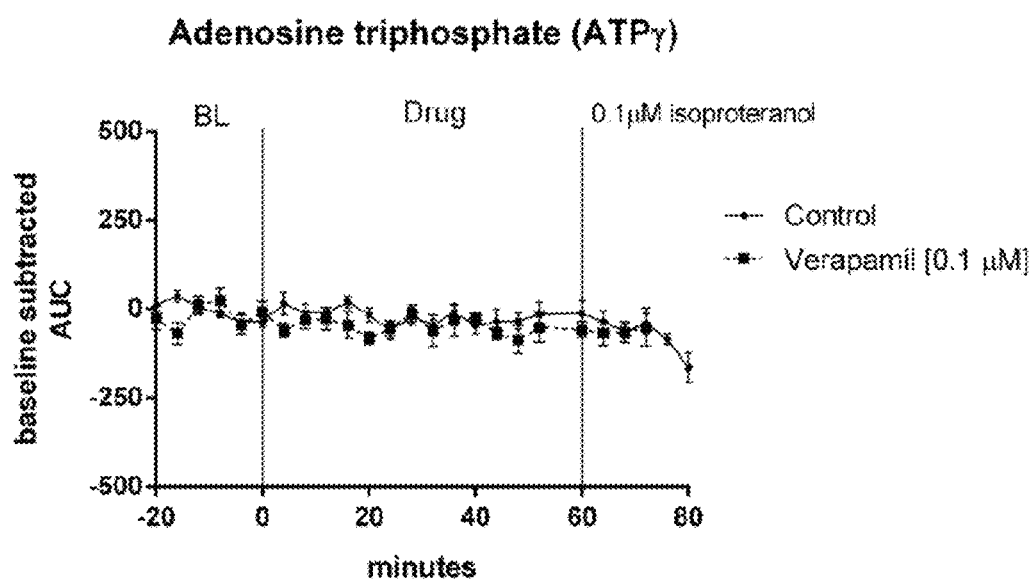
Figure 5A:
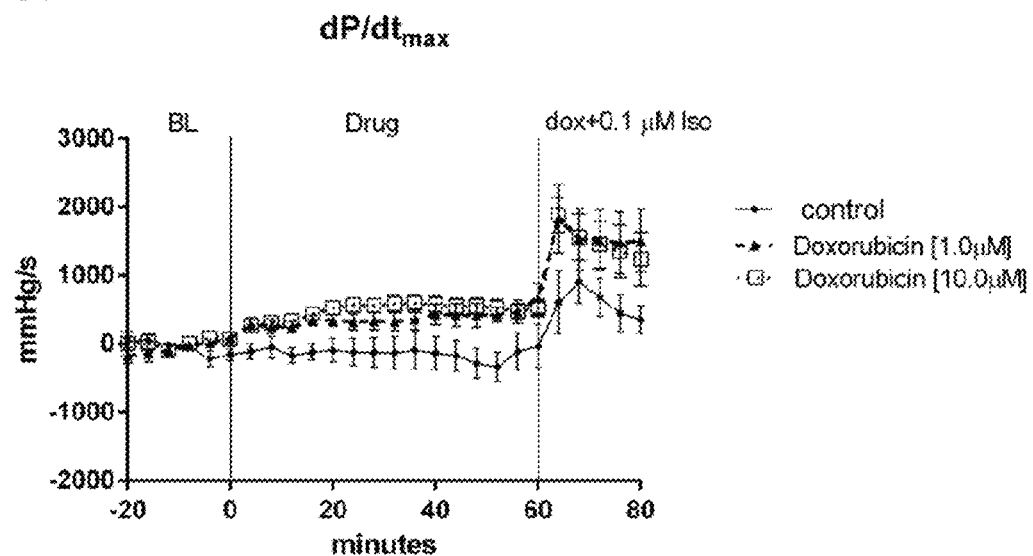
FIG. 5a-d. Effects of doxorubicin (1 and 10 uM) on contractility (FIG. 5a) and energetic parameters. Contractility increases (FIG. 5a), Pi decreases (FIG. 5b), PCr decreases (FIG. 5c), and ATP decreases (FIG. 5d). These effects are pronounced in the isoproteranol stress test period.
Figure 5B:
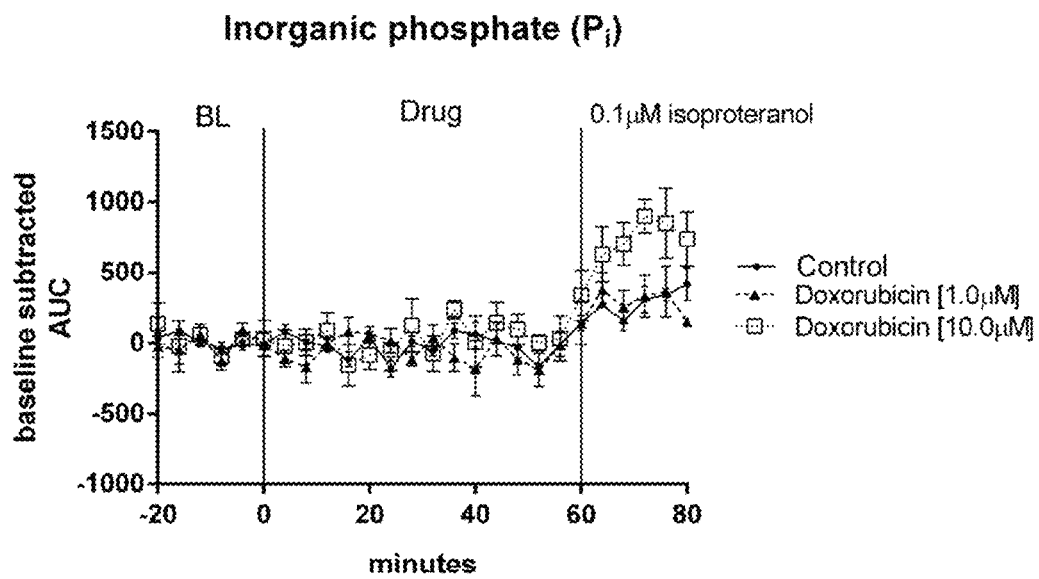
Figure 5C:
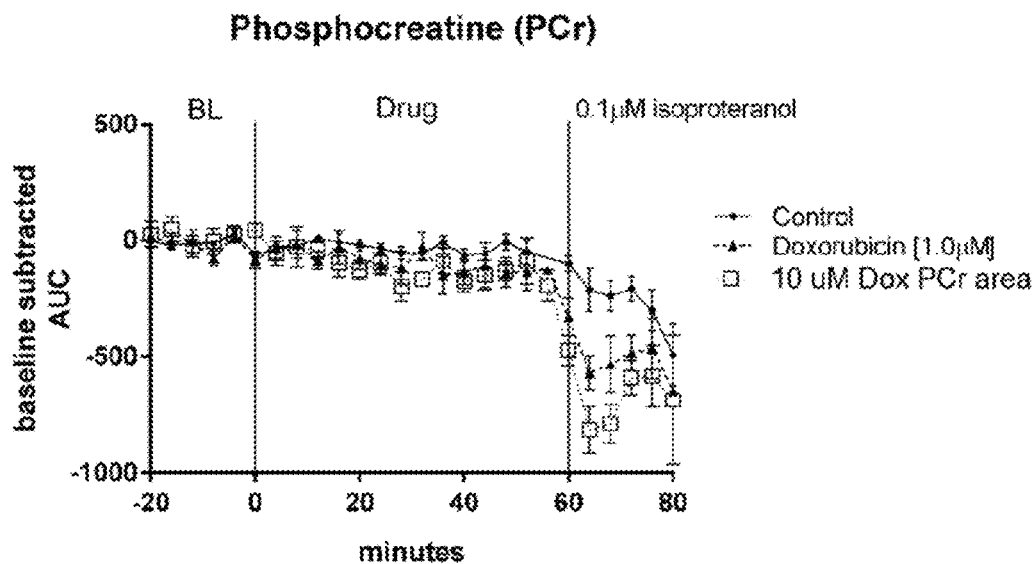
Figure 5D:
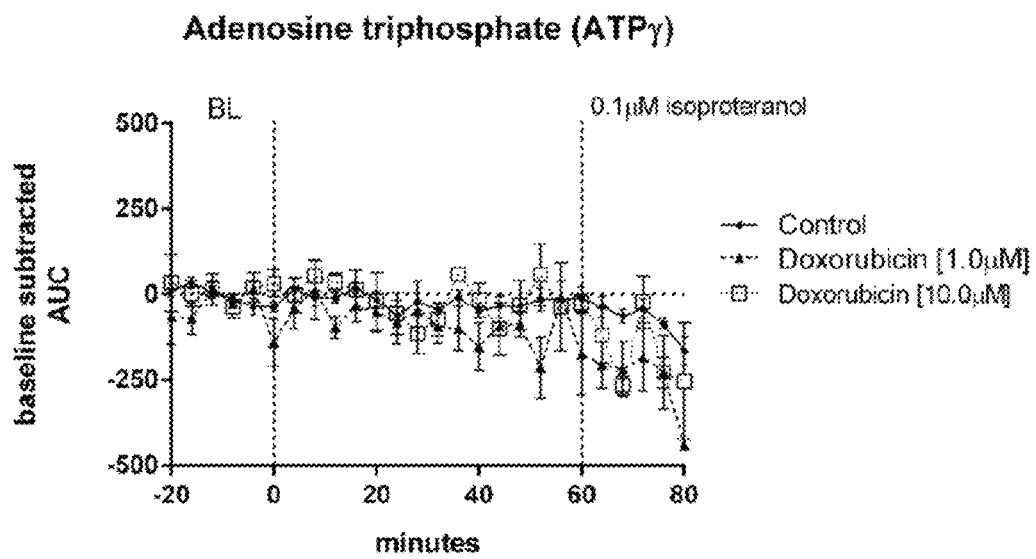

A heart, in this case isolated from rat and perfused using the Langendorff method, is image guided by 1 H magnetic resonance imaging and magnetic resonance spectroscopy is performed for $^{31}P$ found in the high energy phosphogens ATP, phosphocreatine (PCr), and inorganic phosphate (Pi) in an upright 11.7 Tesla NMR at 161.99 MHz (FIGS. 1 and 2).

The energetic spectra from the whole heart was averaged every 4 minutes before and after drug exposure. PCr, ATP alpha, beta, and gamma, and Pi peak height and area, and pH calculated from the resonance shift in Pi (pHi=pK+log [(go−gB)/gA−go)] (Hayashi Y. et al J Appl Physiol 1993) are done using Para Vision, Bruker Inc. (Billerica, Mass.) and ITT Visual Information Solutions (Boulder, Colo.). Heart contractility (left ventricular pressure) and heart rate is simultaneously acquired on an Emka IOX data acquisition system.

$^{31}P$ spectra is acquired for 20 minutes prior to drug application. The drug of interest is then applied for 1 hour followed by a 20 minute stress test using 0.1 um isoproteranol (a beta agonist) in the presence of the drug which causes increased contractility, relaxation, heart rate, and increased conduction velocity. This step is done to test the energy reserve of the heart after drug application. Two negative controls are used, consisting of a group exposed only to modified krebs buffer, and verapamil, a drug that reduces contractility but does not affect cardiac energetic. As a positive control, we use FCCP, a mitochondrial uncoupler that inhibits mitochondrial oxidative phosphorylation by disrupting the mitochondrial protein gradient. We then use doxorubicin (at 1 and 10 uM), a chemotherapeutic compound known to cause latent cardiotoxicity and shown previously to affect mitochondrial function and reduce phosphocreatine/ATP beta levels in vivo and ex vivo (Maslov, M. Y., Chacko, V. P., Hirsch, G. A., Akki, A., Leppo, M. K., Steenbergen, C. and Weiss, R. G. Reduced in vivo high-energy phosphates precede adriamycin-induced cardiac dysfunction. *American Journal of Physiology—Heart and Circulatory Physiology.* 299:H332-H337.2009; Bittner, V., Reeves, R., Digerness, S., Caulifield, J. and Pohost, G. 1991. $^{31}P$ NMR spectroscopy in chronic adriamycin cardiotoxicity. *Magn Reson Med.* 17:69-81, 1991).

We found that in the krebs control group contractility parameters remained stable until the stress test, where they increased. Looking only at Pi, ATPγ, and PCr peaks, we found that Pi and ATPγ peak were stable until the stress test where Pi increased and ATPγ decreased. PCr remained relatively stable until around 90 minutes where they declined slightly, until the stress test where they dramaticly declined. FCCP caused declines in contractility, PCr, and ATPγ, but did not affect Pi. During the stress test period, contractility increased slightly, there was no effect on Pi, PCr dropped slightly, ATPγ declined further (FIG. 3). This demonstrates that FCCP reduced energy stores to the heart, affecting contractility and when it was treated with isoproteranol, it could not respond the same way a normal heart can because its energy reserves were so low.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of determining cardiac toxicity of a compound of interest, comprising the steps of
   a. optionally, i) determining from a heart or cardiac cell of a mammal peak levels of one or more indicators of cardiac energetics selected from inorganic phosphate, phosphocreatine, ATPγ, or a combination thereof; and ii) one or more indicators of cardiac function selected from contractility, relaxation, heart rate, conduction velocity, or a combination thereof, before administration of said compound of interest to the heart or cardiac cell;

b. contacting said heart or cardiac cell of a mammal with said compound of interest;

c. measuring after step (b), i) peak levels of said one or more indicators of cardiac energetics after administration of said compound of interest to the heart or cardiac cell of the mammal; and, optionally, ii) one or more indicators of cardiac function selected from contractility, relaxation, heart rate, conduction velocity, or a combination thereof;

d. contacting said heart or cardiac cell of said mammal previously contacted with said compound of interest, after step (c) with an agent known to cause an increase in cardiac function, said cardiac function selected from contractility, relaxation, heart rate, conduction velocity, or a combination thereof;

e. measuring after step (d), i) peak levels of said one or more indicators of cardiac energetics after administration of said agent known to cause an increase in cardiac function; and, optionally ii) one or more indicators of cardiac function selected from contractility, relaxation, heart rate, conduction velocity, or a combination thereof;

f. comparing the levels of said one or more indicators obtained in step (c) with the levels of said one or more indicators obtained in step (e);

wherein a decrease in one or more indicators of cardiac energetics as measured in step (c) as compared to step (e) indicates that the compound of interest does, or is likely to have, cardiotoxic properties; and wherein levels of said one or more indicators of cardiac energetics are obtained using 31P NMR.

2. The method of claim 1, wherein a decrease in phosphocreatine and ATPγ indicates that said compound of interest is cardiotoxic.

3. The method of claim 1, wherein said agent known to cause an increase in cardiac function comprises a beta adrenergic agonist.

4. The method of claim 1, wherein steps (b) and (d) further comprise the step of measuring a biomarker known to be associated with cardiotoxicity.

5. The method of claim 4, wherein said biomarker comprises TNFα.

6. The method of claim 1, wherein the period of time between step (b) and step (d) is at least 5 minutes.

7. The method of claim 1, wherein the period of time between step (b) and step (d) is at least 10 minutes.

8. The method of claim 1, wherein the period of time between step (b) and step (d) is at least 20 minutes.

9. The method of claim 1, wherein the period of time between step (b) and step (d) is at least 30 minutes.

10. The method of claim 1, wherein the period of time between step (b) and step (d) is at least 45 minutes.

11. The method of claim 1, wherein the period of time between step (b) and step (d) is at least one hour.

* * * * *